(12) United States Patent
Jensen

(10) Patent No.: US 6,796,967 B2
(45) Date of Patent: Sep. 28, 2004

(54) INJECTION NEEDLE ASSEMBLY

(75) Inventor: James U. Jensen, Salt Lake City, UT (US)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 128 days.

(21) Appl. No.: 10/080,938

(22) Filed: Oct. 22, 2001

(65) Prior Publication Data

US 2003/0078546 A1 Apr. 24, 2003

(51) Int. Cl.[7] .............................................. A61M 5/32
(52) U.S. Cl. ....................... 604/197; 604/192; 604/201; 604/199; 604/244; 604/411; 604/905
(58) Field of Search ................. 604/87–90, 110, 604/111, 117, 136, 138, 139, 135, 156, 157, 192, 195–199, 201–205, 232, 244, 256, 263, 411, 414–415, 905; 141/329, 330, 286, 19, 382–386; 606/182

(56) References Cited

U.S. PATENT DOCUMENTS

| | | | |
|---|---|---|---|
| 4,178,928 A | | 12/1979 | Tischlinger |
| 4,227,528 A | * | 10/1980 | Wardlaw .................... 604/139 |
| 4,258,713 A | | 3/1981 | Wardlaw |
| 4,564,054 A | | 1/1986 | Gustavsson |
| 4,624,660 A | | 11/1986 | Mijers et al. |
| 4,968,302 A | | 11/1990 | Schluter et al. |
| 5,342,319 A | | 8/1994 | Watson et al. |
| 5,391,151 A | | 2/1995 | Wilmot |
| 5,409,466 A | | 4/1995 | Watson et al. |
| 5,419,773 A | | 5/1995 | Rupp |
| 5,527,287 A | * | 6/1996 | Miskinyar .................... 604/135 |
| 5,549,558 A | | 8/1996 | Martin |
| 5,609,577 A | | 3/1997 | Haber et al. |
| 5,616,128 A | | 4/1997 | Meyer |
| 5,762,634 A | | 6/1998 | Davis |
| 5,873,856 A | * | 2/1999 | Hjertman et al. ........... 604/117 |
| 5,964,739 A | * | 10/1999 | Champ ....................... 604/263 |
| 6,045,534 A | * | 4/2000 | Jacobsen et al. ............ 604/156 |
| 6,086,562 A | | 7/2000 | Jacobson et al. |
| 6,090,091 A | * | 7/2000 | Fowles et al. ............... 604/403 |
| 6,102,896 A | * | 8/2000 | Roser .......................... 604/218 |
| 6,165,155 A | * | 12/2000 | Jacobsen et al. ............ 604/156 |
| 6,183,446 B1 | * | 2/2001 | Jeanbourquin ............... 604/198 |
| 6,203,529 B1 | * | 3/2001 | Gabriel et al. ............... 604/192 |
| 6,387,078 B1 | * | 5/2002 | Gillespie, III ............... 604/181 |
| 6,391,003 B1 | * | 5/2002 | Lesch, Jr. .................... 604/110 |
| 6,547,764 B2 | * | 4/2003 | Larsen et al. ................ 604/192 |

\* cited by examiner

Primary Examiner—Brian L. Casler
Assistant Examiner—Cris L. Rodriguez
(74) Attorney, Agent, or Firm—TraskBritt

(57) ABSTRACT

A needle assembly for use with an injection device including a pair of housing members slidably coupled with one another. A needle is structurally attached to one of the housing members such that it is positioned within the two housing members. A first membrane is disposed on an opening of one housing member and a second membrane is disposed on an opening of the other housing member such that the needle is concealed from the view and access of a user thereof. The needle assembly may be contracted by sliding one housing member relative to the other causing the needle to penetrate one of the membranes and administer an injection into or below the skin of the user. Additionally, one or more locking mechanisms may be incorporated to prevent inadvertent needle sticks.

30 Claims, 13 Drawing Sheets

INJECTION NEEDLE ASSEMBLY

BACKGROUND OF THE INVENTION

1. Field of the Invention

The present invention relates generally to injection devices and methods and, more specifically, to needle assemblies for use in injection devices and methods directed to improving compliance with regard to the self administration of drugs.

2. State of the Art

Injection devices are commonly utilized for the delivery of a substance to a patient. Such injection devices conventionally include a container, such as a syringe or a carpule, for holding the material to be injected, means for measuring or dosing the material, a needle or other delivery device for delivering the material into or beneath the patient's skin, and an actuator for moving the material through the delivery device and into the patient.

Various types of injection devices are available, including devices configured and intended for self-administration or self-injection. Self-injection devices may be commonly used for administering, for example, insulin to a diabetic. Additionally, new drugs and medical treatments are suited for self administration via injection.

An issue associated with treatment involving self-injection is ensuring patient compliance. For example, even though a treatment has been prescribed, a patient may not fully comply for various reasons, including, for example, the inability to properly operate the injection device due to its complexity or due to the physical limitations of the patient. Additionally, patient compliance is often difficult to ensure simply because of the patient's apprehension in injecting a needle into their own skin.

Another issue associated with self-injection includes the handling of the injection device and the possibility of inadvertent needle sticks either prior to or after the administration of the injection. Such inadvertent needle sticks further add to the apprehension of the user.

One device intending to deal with such issues is disclosed in U.S. Pat. No. 5,609,577 to Haber et al., issued Mar. 11, 1997, and which is incorporated by reference herein. The Haber patent discloses a device which includes a self-locking mechanism to help prevent inadvertent needle sticks. Specifically, the Haber patent discloses the use of a shield formed about the needle to hide the needle from view of a patient. However, the device disclosed by the Haber patent still allows for view of the needle through the end of the shield and, further, allows view and access to the needle during preparation, as the needle needs to be removed and replaced for each individual injection. Thus, even though users may not see the needle immediately prior to injection, they may still view the needle while installing or removing a needle or may view an installed needle by looking through the end of the shield. Thus, while the device disclosed by the Haber patent may be useful in hiding the needle from the view from a patient receiving an injection administered by another, those who are practicing self-injection will ultimately view the needle and may suffer apprehension leading to noncompliance in some individuals. Additionally, while the Haber patent discloses a locking mechanism to prevent inadvertent needle sticks when the needle is installed on the injection device, such needle sticks may still occur during the removal and replacement of the needle from the injection device.

In view of the shortcomings in the art, it would advantageous to provide a needle assembly which improves user compliance by concealing the injection needle from the access and view of a user. Additionally, it would be advantageous to configure such a needle assembly for removable attachment to an injection device. Further, it would be advantageous to provide a needle assembly with one or more locking mechanisms to prevent inadvertent sticks while the needle is coupled to the injection device and also during handling of the needle assembly while it is uncoupled from the injection device.

BRIEF SUMMARY OF THE INVENTION

In accordance with one aspect of the invention, an injection needle assembly is provided. The needle assembly includes a first housing member which has an opening defined therein. A first membrane is disposed on the first housing member so as to cover its opening. A second housing member is coupled to the first housing member and also has an opening defined therein. A second membrane is disposed on the second housing member so as to cover its respective opening. A needle is disposed within the first and second housing members such that the needle is concealed from a user thereof by the first and second housing members and the first and second membranes.

The needle assembly may further be configured such that, upon coupling with an injection device, the first membrane is displaced inwardly of the needle assembly causing the needle to penetrate therethrough.

Additional features may also be incorporated with the needle device, such as safety locking mechanisms. For example, a locking mechanism may be incorporated whereby the first and second housing members are prevented from moving relative to each other prior to coupling of the needle assembly with an injection device. A separate locking mechanism may be utilized to prevent inadvertent actuation of the needle assembly after its coupling with an injection device but prior to intended employment of the injection device.

According to another aspect of the invention, a needle assembly includes a first housing member configured to be removably coupled with an injection device. A first membrane is disposed on and covers an opening at the proximal end of the first housing member. A second housing member is coupled with the first housing member and is longitudinally slidable relative to the first housing member. A second membrane is disposed upon and covers an opening formed in the second housing member. A needle is rigidly fixed to the first housing member disposed within the first and second housing members and concealed by the first and second membranes.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
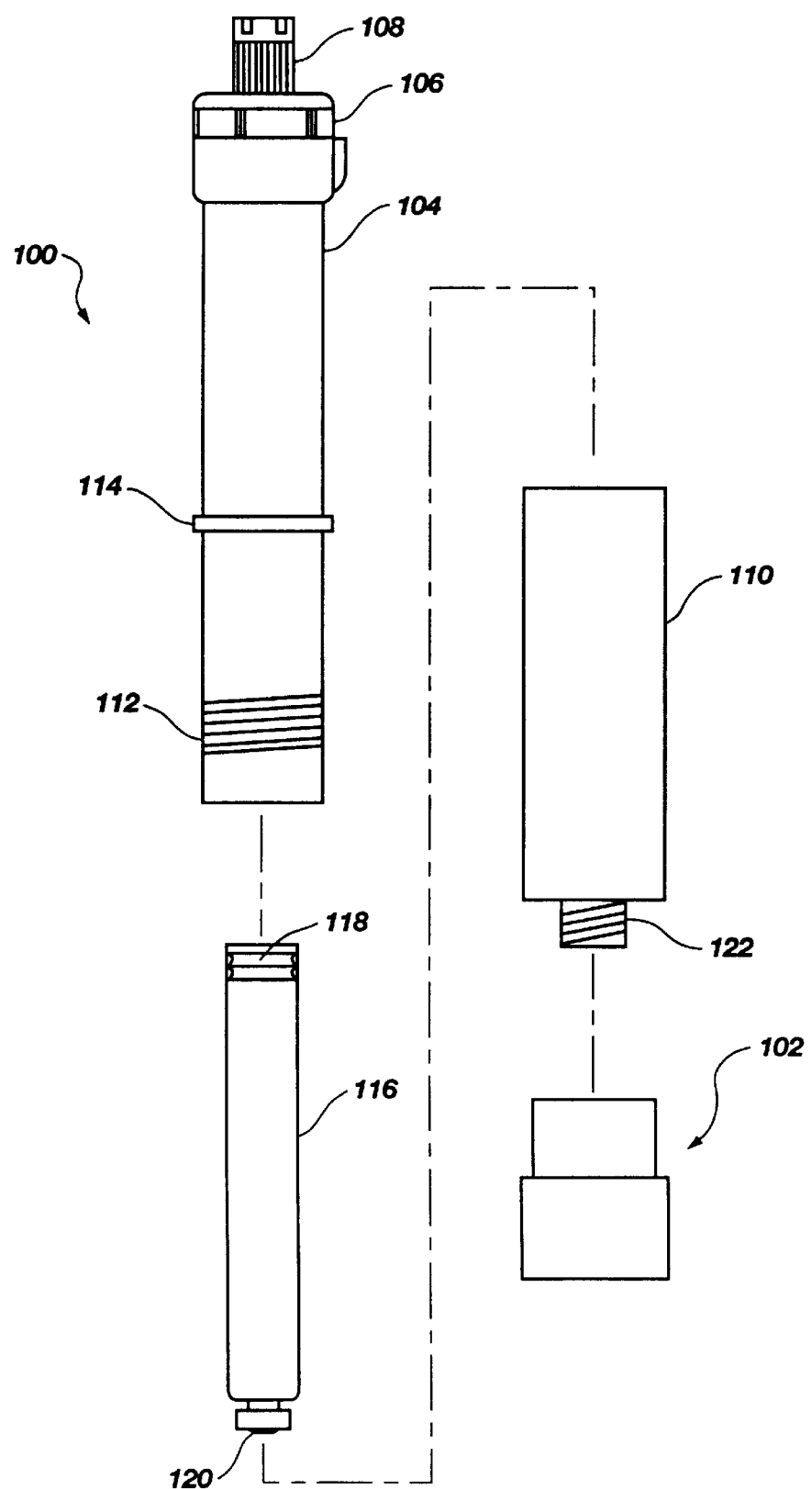
FIG. 1 is an exploded view of an injection device which incorporates a needle assembly according to one aspect of the invention.

Referring to FIG. 1, an exemplary injection device 100 is shown including a needle assembly 102 for coupling thereto. It is noted that the injection device 100 depicted herein is a pen-type injection device. However, other injection devices may be suitable for use in conjunction with the needle assembly 102 of the present invention as will be understood and appreciated by those of ordinary skill in the art.

The injection device 100 includes an upper portion 104 having a dosing ring 106 and an actuator 108 which are coupled to a plunger device (not shown in FIG. 1) internally housed in the upper portion 104. A lower portion 110 is configured to be removably coupled with the upper portion 104 by means of mating threads 112 externally formed on the upper portion 104 and internally formed on the lower portion 110. A collar 114 is formed on the upper portion 104 which abuts the lower portion 110 and acts as a stop between the two portions 104, 110 during assembly.

Prior to assembly of the upper and lower portions 104 and 110, a carpule 116 is placed in the interior of the two portions 104 and 110. The carpule 116 is a container filled with a drug in lyophilized form for subsequent mixture and delivery via injection. A first stopper 118 is located at a proximal end of the carpule 116 and is slidably and sealingly disposed therein. The first stopper 118 is configured to abut the plunger device housed in the upper portion 104 (see FIG. 3A) such that the plunger may motivate the first stopper towards the distal end of the carpule 116. Motivation of the first stopper 118 causes the lyophilized drug to be mixed with a liquid within the carpule and subsequently dispenses the drug when the actuator 108 is properly operated as is understood by those of ordinary skill in the art. A second stopper 120, is sealingly disposed within the distal end of the carpule 116 and is configured to receive a needle therethrough (see FIG. 3A) for delivery of the drug. While the substance for injection is disclosed as being a drug in lyophilized form mixed with a liquid prior to injection, the substance may include any material in any form which is suitable for delivery through an injection type device.

The needle assembly 102 is configured to be coupled to the lower portion 110 such as by mating threads 122. In the exemplary injection device 100, the needle assembly 102 is designed to be a disposable device, while the remainder of the injection device 100 is configured to be utilized multiple times, each use being performed with a new sterile needle assembly 102 and a new drug-containing carpule 116. However, it is contemplated that the entire injection device 100 may be disposable. Alternatively, the drug-containing carpule 116 need not be replaced after each use, as the injection device 100 may be configured for multiple doses. Such a multiple dose injection device may include additional features to help ensure adequate sterility of the needle assembly and, thus, may render the needle assembly a multiuse device as well.

Figure 2:
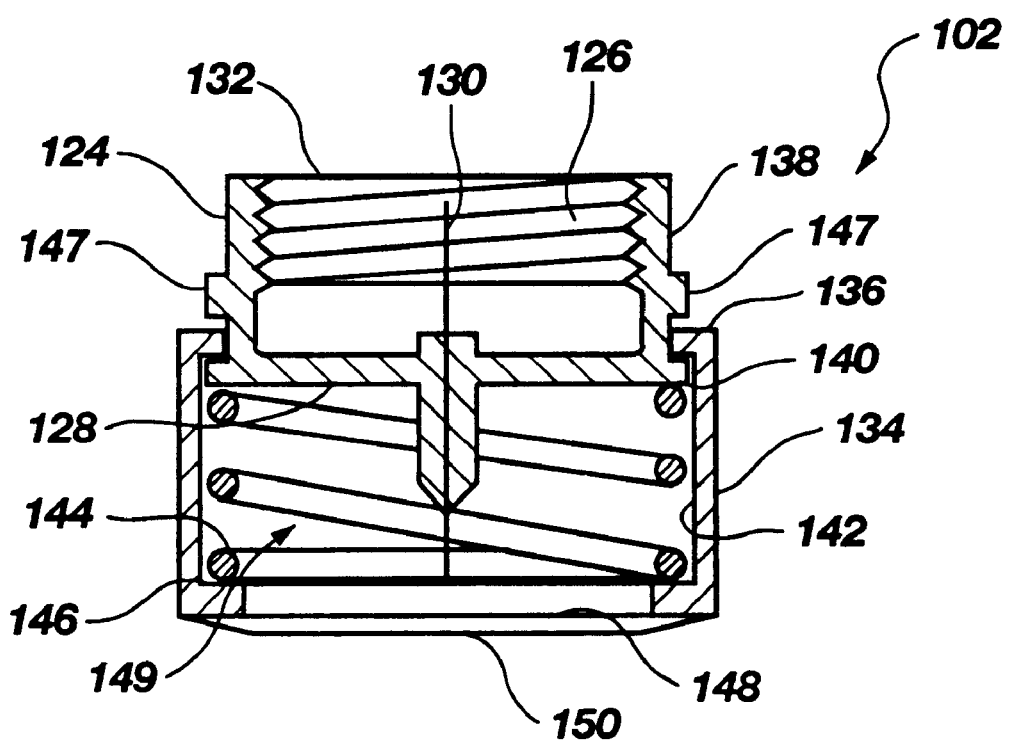
FIG. 2 is a sectional view of the needle assembly according to one embodiment of the invention.

Referring to FIG. 2, a cross section of the needle assembly 102 is shown. The needle assembly 102 includes an upper housing member 124 having internal threads 126 for coupling with the mating threads 122 of the lower portion 110 of the injection device 100. The upper housing member 124 also has a support structure 128 for rigidly holding a hypodermic needle 130 relative to the upper housing member 124. A first membrane 132 covers the proximal and of the upper housing member 124 and conceals the needle 130 from access and view of a user prior to coupling of the needle assembly 102 with an injection device 100. The first membrane 132 may also conceal the needle 130 from access and view of a user after decoupling the needle assembly 102 from the injection device 100 depending on the type of first membrane 132 utilized.

A lower housing member 134 is slidably coupled to the upper housing member 124. The lower housing member 134 has a first collar 136 which is slidably positioned against the exterior side wall 138 of the upper housing member 124. A flange 140 on the upper housing member 124 is located internally of and is configured to be slidable relative to the interior wall 142 of the lower housing member 134. The flange 140 abuts the first collar 136 when the needle assembly 102 is in the extended position (as shown) and keeps the lower housing member 134 from being separated from the upper housing member 124. A biasing member 144, shown as a coil spring, is disposed between the flange 140 and a second collar 146 located at the distal end of lower housing member 134. The biasing member 144 is configured to keep the needle assembly 102 in an extended position prior to and after an injection. In other words, the upper housing member 124 and the lower housing member 134 are pushed away from each other, causing an abutment of the flange 140 with the first collar 136, unless a sufficient force is applied to contract the needle assembly 102. In a particular embodiment, a pair of protuberances 147 may be formed on the exterior surface of the upper housing member 124 as part of a locking mechanism which shall be described in greater detail below.

As will be recognized by those of skill in the art, the biasing member 144 may be placed in a different location to effect the biasing of the upper housing member 124 away from the lower housing member 134. For example, it may be desirable in certain instances to isolate the biasing member 144 from the hypodermic needle 130. In such a case, the biasing member 144 may be removed from the internal cavity 149 formed in the lower housing member 134 and, for example, placed between the flange 140 of the lower housing member 134 and the first collar 136 of the upper housing member 124. In such a configuration the biasing member 144 would expand or elongate, rather than contract, upon the downward displacement of the upper housing member 124 relative to the lower housing member 134. Of course, other configurations regarding the placement of the biasing member 144 relative to the upper and lower housing members 124 and 134 are also contemplated.

A second membrane 148 covers the distal end of the lower housing member 134 concealing the distal end of the needle 130 from access and view of the user prior to and subsequent injection of the needle 130 into an area of the user's skin. A pad 150, such as a gauze-type pad, may be disposed on the second membrane 148 and may be treated with an antiseptic and/or anesthetic for application to the area of skin which will receive the injection. Alternatively, the second membrane 148 may include a bladder which contains antiseptic and/or anesthetic which may be released when the second membrane 148 is punctured by the needle 130.

The upper and lower housing members 124, 134 may be made of various materials, but are desirably made of plastic since the needle assembly 102 may be designed for single use and, thus, may be disposed after and injection therewith. Forming such members out of plastic allows for economical production and offers certain sterility qualities desirable in a medical device. It is additionally desirable to form the housing members 124, 134 of an opaque material such that the needle 130 may not be viewed through the housing members 124, 134.

The membranes 132, 148 may be formed of any number of materials. For example, latex may be used to form either or both of the membranes 132, 148. Similarly, either or both membranes 132, 148 may be formed of a material such as polytetrafluoroethylene (PTFE, sometimes referred to as Teflon). It is noted that the first membrane 132 need not be formed from the same material as the second membrane 148.

Additionally, the upper and lower housing members 124, 134 are contemplated as being generally cylindrical in shape. Such shaping lends itself to certain aspects of manufacturing the needle assembly 102. However, such a configuration should not be considered limiting in any sense. The upper and lower housing members 124, 134 can be made in other geometrical configurations, if so desired.

The needle assembly 102 is configured such that the needle 130 can not be accessed or viewed by a user during preparation of the injection device 100, during use, and upon disposal of the needle assembly 102 after an injection. Concealment of the needle 130 from the view of a user is effected by the overall configuration, including the ends of the needle assembly 102 being covered by the first and second membranes 132 and 148. Access to the needle 130 by a user may be prevented by minimizing the internal diameters of the upper and lower housings 124 and 134 in conjunction with the placement of the needle ends at a sufficient distance relative to the membranes 132 and 148 while the needle assembly 102 is in the extended position.

The proximal end of the needle 130 is never exposed to the user and only penetrates the first membrane 132 when coupled to an injection device 100. As discussed hereafter, this occurs due to the inward displacement of the first membrane 132 during coupling of the needle assembly 102 to the injection device 100. In the case where the first membrane 132 is formed of a resilient material (e.g., latex) the first membrane will return to its original position again covering the needle 130 and only exhibit a small puncture formed by the needle 130. Alternatively, the membrane may be formed of a material subject to plastic deformation (e.g., PTFE) which will serve to conceal the needle 130 prior to coupling of the needle assembly 102 and the injection device 100. The proximal end of the needle 130 is only exposed to the user upon proper employment of the injection device 100 and then is only exposed to a particular area of the user's skin which is to receive the injection.

Figure 3A:
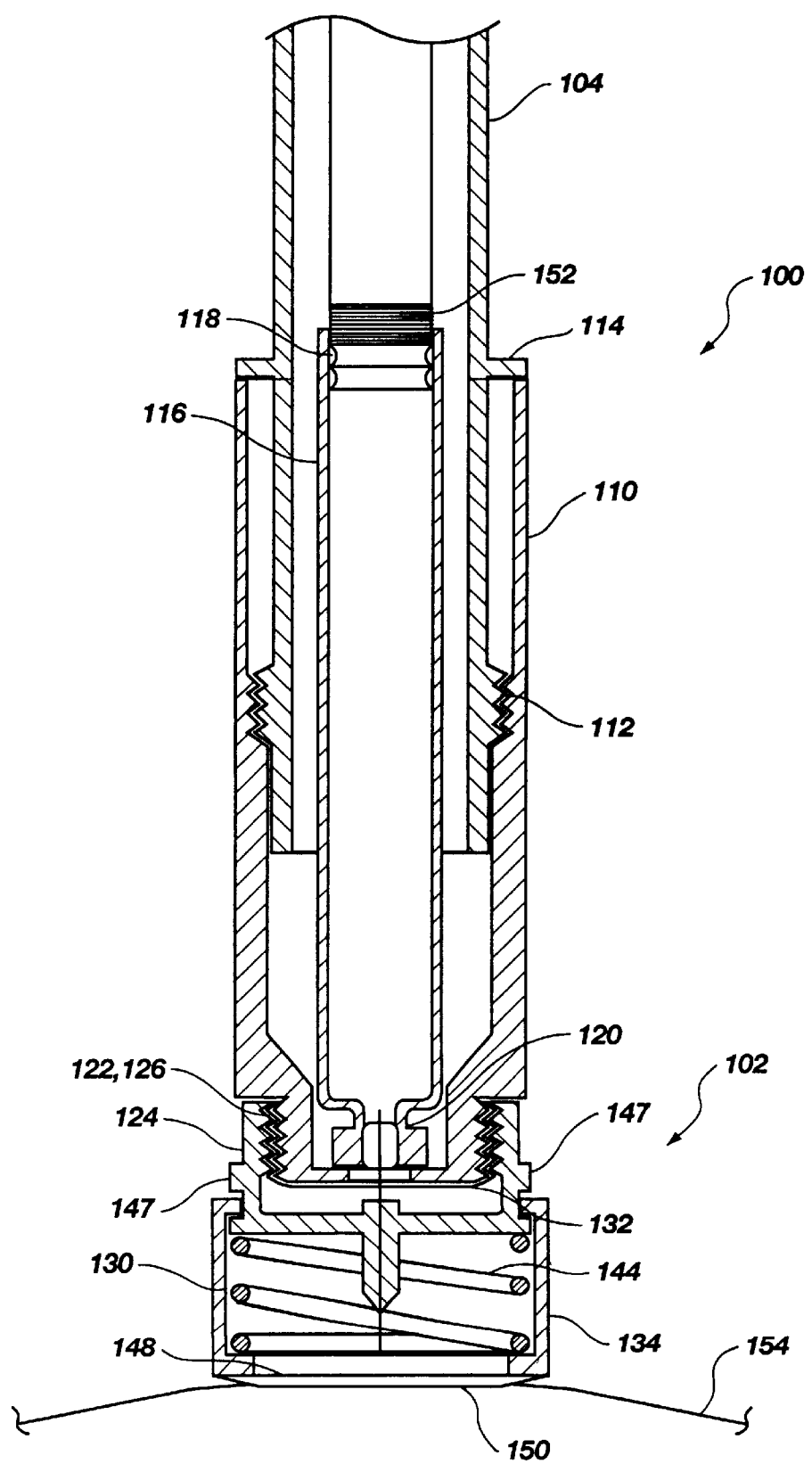
FIGS. 3A and 3B are cross-sectional views of the needle assembly of FIG. 2 operably coupled with an injection device.
Figure 3B:
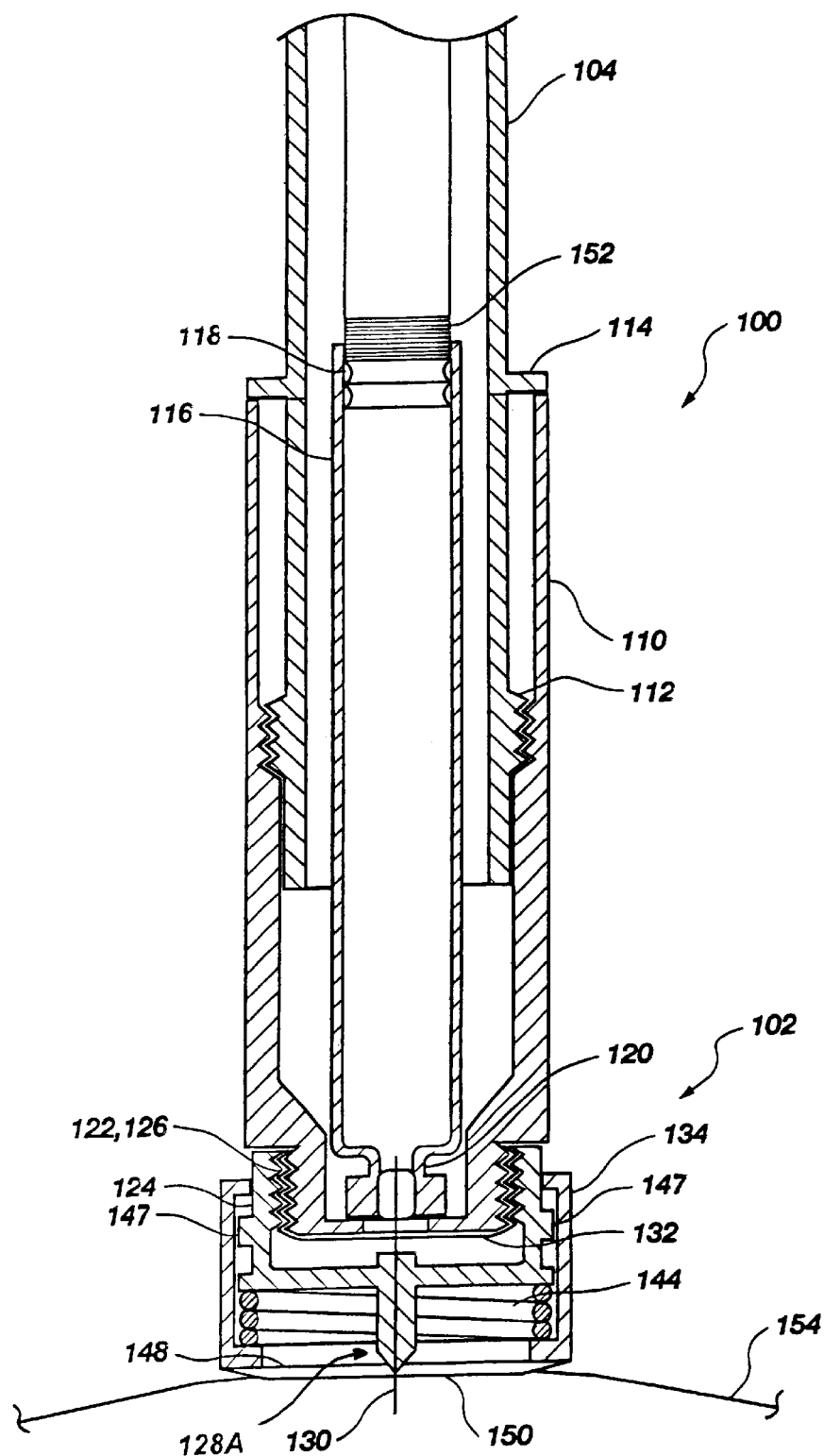

Referring now to FIGS. 3A and 3B, the operation of the needle assembly 102 in conjunction with an injection device 100 is illustrated. A cross-sectional view of the injection device 100 is depicted with the carpule 116 loaded therein and a plunger device 152 abutting the first stopper 118 at the proximal end of the carpule 116. The needle assembly 102 is coupled to the injection device 100 by way of the mating threads 122 and internal threads 126. It can be seen that upon coupling of the needle assembly 102 and the injection device 100, the first membrane 132 is displaced inwardly relative to the upper housing member 124. This causes the needle 130, which is fixed relative to the upper housing member 124, to penetrate the first membrane 132 and expose the proximal end of the needle 130 to the interior of the injection device 100. More particularly, the proximal end of the needle 130 further penetrates the second stopper 120 at the distal end of the carpule 116, exposing the needle 130 to any drug or fluid contained by the carpule 116. As understood by those of ordinary skill in the art, the second stopper 120 is formed of a material which allows a seal to be formed about the penetrating needle 130, such that fluid may be transferred through the needle 130 without leakage between the second stopper 120 and the needle 130.

It is noted that in the exemplary embodiment shown in FIGS. 3A and 3B, the first membrane 132 is displaced between the mating threads 122 and internal threads 126 of the injection device 100 and the needle assembly 102, respectively. Proper tolerances of the mating threads 122 and internal threads 126 will allow for secure attachment of the injection device 100 to the needle assembly 102 while also allowing the first membrane 132 to stretch and conform the same to the space between the mating threads 122 and internal threads 126 without tearing, if so desired. Such displacement may also be minimized by designing the connection between the needle assembly 102 and the injection device 100 such that the lower portion 110 of the injection device 100 is minimally inserted within the upper housing member 124 while maintaining a secure connection therebetween. Additionally, other coupling configurations and connection designs may allow for coupling of the needle assembly 102 to the injection device 100 with minimal displacement and or torsion experienced by the first membrane 132.

FIG. 3A shows the injection device 100 and needle assembly 102 positioned against an area of the user's skin 154 prior to penetration of the needle 130 into the user's skin. A pad 150, or other device treated with antiseptic and/or anesthetic, causes the user's skin 154 to be sterilized and/or numbed, as the case may be, prior to penetration by the needle 130. At this stage, the distal end of the needle 130 is still concealed within the needle assembly 102, the biasing member 144 keeping the needle assembly 102 in an extended position and maintaining such extended position until a safety or other locking mechanism is properly disengaged, as discussed in greater detail below herein.

Subsequent disengagement of any locking mechanism, and upon application of a downward force sufficient to overcome the force exerted by the biasing element 144, the needle assembly 102 contracts such that the upper housing member 124 slides within the lower housing member 134, causing the needle 130 to penetrate the second membrane 148, the pad 150, and ultimately the skin 154 of the user, as shown in FIG. 3B. Desirably, the distal end of the support structure 128A is displaced until it contacts the internal surface of the second membrane 148. Upon penetration of the user's skin 154 by the needle 130, the user may deliver the drug or other substance therethrough by proper actuation of the injection device 100 and the needle assembly 102 coupled thereto. It is again noted that the injection device 100 may include mechanisms having various configurations which may be actuated in a variety of manners. However, referring to the exemplary injection device disclosed herein, operation of the actuator 108 (FIG. 1) motivates the plunger device 152 which subsequently pushes downwardly on the first stopper 118. The first stopper 118 travels a predetermined distance within the carpule 116, which distance is related to the dosing amount. The displacement of the first stopper 118 forces a predetermined quantity of drug to flow from the carpule 116 and through the needle 130, delivering the drug into the user's skin 154 of the user. Upon application of an upward force to the injection device 100, the biasing element 144 displaces the lower housing member 134 downward and away from the upper housing element 124. This action returns the needle assembly 102 to the position shown in FIG. 3A and conceals needle 130 within the needle assembly 102 upon removal of the needle assembly 102 from the user's skin 154, leaving only a small puncture in the second membrane 148. The needle 130 remains out of view of the user at all times, thus avoiding any apprehension the user might otherwise experience upon sight of an exposed needle.

Figure 4A:
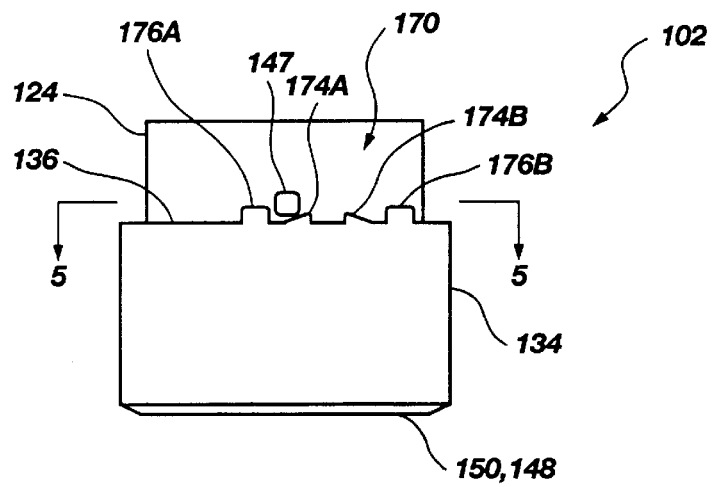
FIGS. 4A–4C are side views of the needle assembly according to another embodiment of the invention.
Figure 4B:
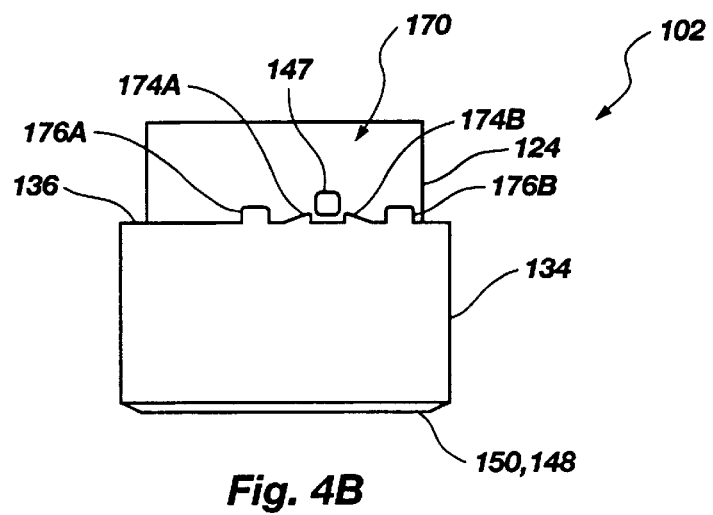
Figure 4C:
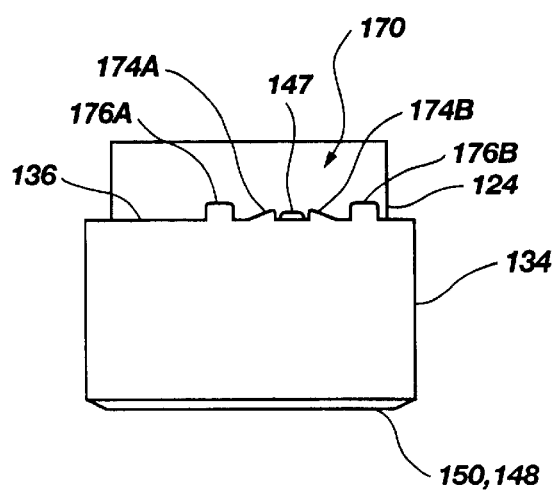
Figure 5:
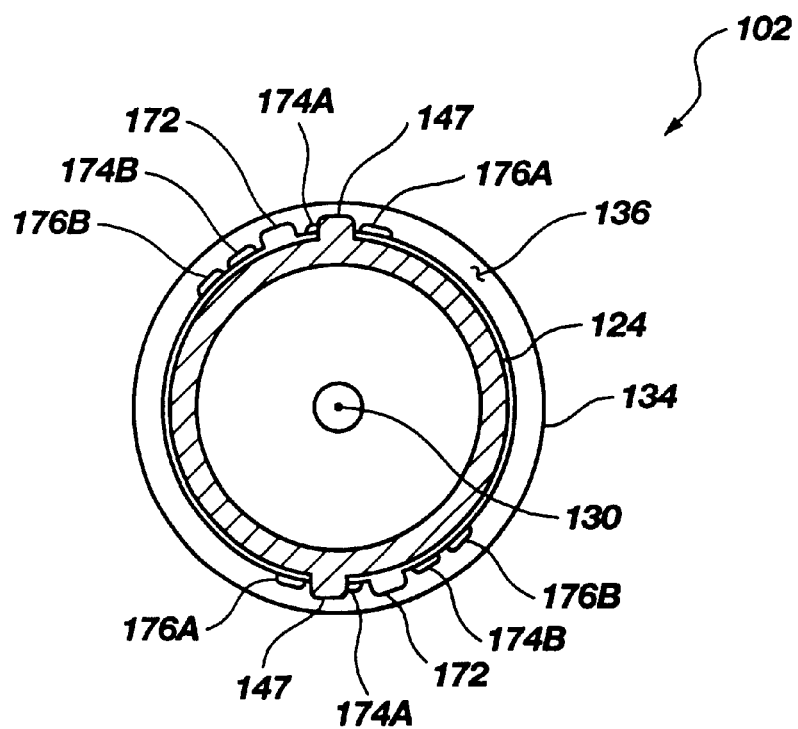
FIG. 5 is a partial sectional view of the needle assembly shown in FIG. 4A.

FIGS. 4A–4C and FIG. 5 depict an exemplary locking mechanism 170 which may be incorporated into the needle assembly 102. Referring particularly to FIGS. 4A and 5, the locking mechanism 170 includes a first set of protuberances 147 formed on the exterior of the upper housing member 124. When in a locked position, the protuberances 147 abut a portion of the lower housing member's 134 first collar 136, keeping the needle assembly 102 from inadvertently contracting. This in turn keeps the needle 130 from protruding through the second membrane 148 and pad 150 until the device is unlocked and the user is prepared to properly employ the injection device 100.

To unlock the needle assembly 102, the upper housing member 124 is rotated relative to the lower housing member 134 until the protuberances 147 are aligned with a corresponding pair of apertures 172 formed in the first collar 136 of the lower housing member 134. Referring to FIG. 4A, this is accomplished by rotating the lower housing member 134 relative to the upper housing member 124 such that the protuberance 147 is displaced to the right and in the position shown in FIG. 4B. Referring to FIG. 5, the needle assembly 102 is unlocked by rotating the lower housing member 134 in the clockwise direction while maintaining the position of the upper housing member 124.

A pair of projections 174A and 174B are formed on the first collar 136 of the lower housing member 134 as part of a safety mechanism to keep the upper and lower and upper housing members 124 and 134 from inadvertently rotating relative to one another into the unlocked position during coupling and uncoupling of the needle assembly to the injection device 100 and removal therefrom. The protuberance 147 is prevented from rotating past the projections 174A or 174B until a sufficient amount of torque is applied to the upper housing member 124 relative to the lower housing member 134, such that the interference between the protuberance 147 and the projections is overcome. The positioning of projections 174A and 174B on each side of the aperture 172 allows the needle assembly 102 to be locked in either a clockwise or counterclockwise rotational direction, which may be advantageous for configuration having threaded connections.

A pair of stops 176A and 176B may be formed on the lower housing member with one being positioned on each side of the aperture 172. The abutment of the protuberance 147 against the stops 176 serves to limit the rotation of the upper housing member 124 relative to the lower housing member 134.

Once the needle assembly 102 is coupled to the injection device 100 and in the unlocked position (such as shown in FIG. 4B), a user may employ the injection device 100 such that the needle assembly 102 contracts with the upper housing member 124 being slidably dispoosed within the lower housing member 134, as shown in FIG. 4C. After the injection device 100 has been used and removed from a user's skin 154, the needle assembly may be placed in the locked position by rotating the lower housing member 134 relative to the upper housing member 124 in the reverse direction as required for unlocking the needle assembly 102. The needle assembly 102 may then be safely removed without apprehension of inadvertent pricking of the user from either end of the needle assembly 102.

Figure 6:
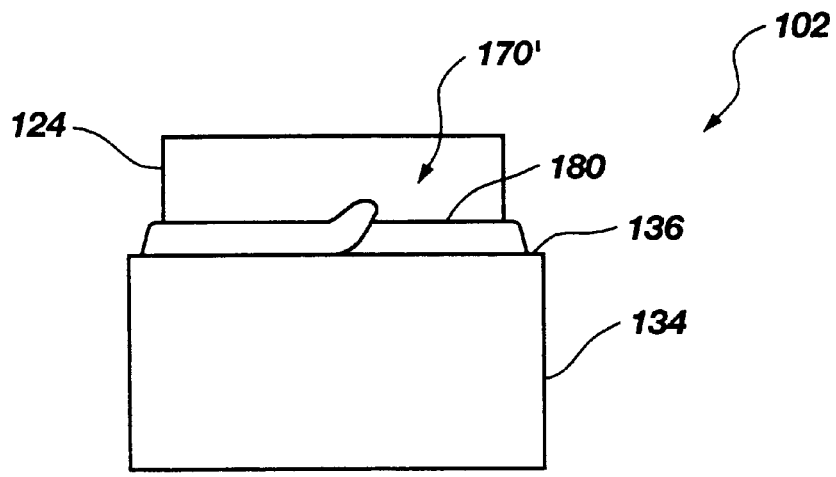
FIG. 6 is a side view of the needle assembly according to another embodiment of the invention.

Referring to FIG. 6, an alternative locking mechanism 170' for the needle assembly 102 is shown. A disposable collar 180 is removably adhered to the exterior surface of the lower housing member 124 abutting the first collar 136 of the lower housing member 134. Being adhered to the upper housing member 124, the disposable collar 180 keeps the needle assembly 102 from contracting by providing an abutment past which the lower housing member 134 may not slide. When the needle assembly 102 is affixed to the injection device 100 and prepared for use, the user may remove the disposable collar 180 by pulling outwardly on the aperture 172 with sufficient force to overcome the adherence of the disposable collar 180 to the upper housing member 124. It is noted that such a disposable collar 180 only provides protection against inadvertent contraction of the needle assembly 102 during coupling of the needle assembly 102 with the injection device 100 prior to injection, but not during removal of the needle assembly 102 subsequent to an injection. However, during removal of the needle assembly 102 it is likely that the needle assembly 102 will be subjected to a downward force in a manner which opposes the contraction thereof. In the needle assembly shown in FIG. 6, the lower housing member 134 will likely be subjected to a downward force sufficient to cause the first collar 136 of the lower housing member 134 to remain in abutting contact with the flange 140 of the upper housing member 124. Thus, since inadvertent contraction of the needle assembly 102 is more likely to occur during installation of the needle assembly 102 than during its removal, a disposable collar 180, or similar mechanism, may adequately protect against such inadvertent contraction.

It is also noted that a disposable collar 180 also serves as an indication of sterility. The existence of the disposable collar 180 would indicate to a user that the needle assembly 102 had not been previously used, while absence of the disposable collar 180 would indicate otherwise. Thus, if desired, the disposable collar 180 could be combined with other locking mechanisms, such as that shown in FIGS. 4A–4C and FIG. 5, allowing the needle assembly 102 to be nondisposable, if so desired, thereby providing a locking of the needle assembly 102 prior to and subsequent to an injection. The combination can also provide an indication of sterility to the user or serve as an added safety feature to prevent accidental needle sticks prior to coupling the needle assembly 102 with the injection device 100.

It is noted that such locking mechanisms 170, 170' are exemplary and variations on the types of locking or safety mechanisms used are contemplated as being within the scope of the invention. As discussed in greater detail below, such mechanisms may include, without limitation, a second similar or different locking mechanism associated with the attachment end of the needle assembly in a manner intended to provide protection against inadvertent compression before attachment and during and after detachment of the needle assembly from the injection device.

Figure 7:
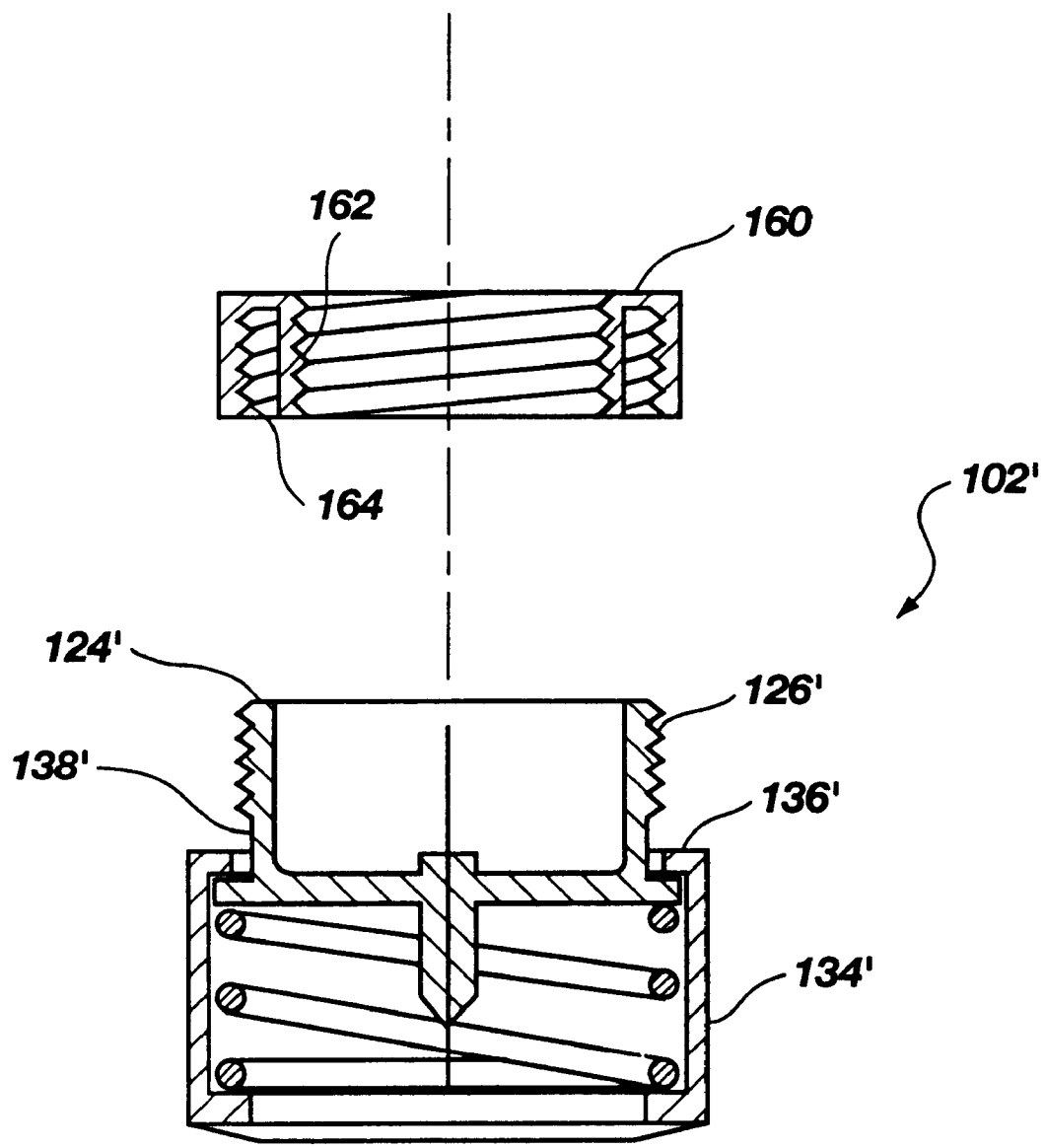
FIG. 7 is an exploded cross-sectional view of the needle assembly with an associated coupling adapter.

Referring to FIG. 7, an alternative embodiment of the needle assembly 102' having a coupling adapter 160 is disclosed. As shown with the previous embodiment, the injection device 100 may utilize external mating threads 122 (shown in FIGS. 1, 3A and 3B) for coupling of the needle assembly 102' to the injection device 100. In such a case, it may be desirable to provide a coupling adapter 160 so that the first membrane 132 need not be located between mating thread 122 portions. The coupling adapter 160 includes a first set of threads 162 for attachment to the injection device 100 and a second set of threads 164 for coupling with the needle assembly 102'. The needle assembly 102' may employ an external set of threads 126' on the upper housing member 124', rather than the internal threads of the previously described embodiment. It is further noted that the first collar 136' of the lower housing member 134' is spaced away from the exterior side wall 138' of the upper housing member 124' so as to clear the coupling adapter 160 when the same is assembled and in a contracted position.

Figure 8:
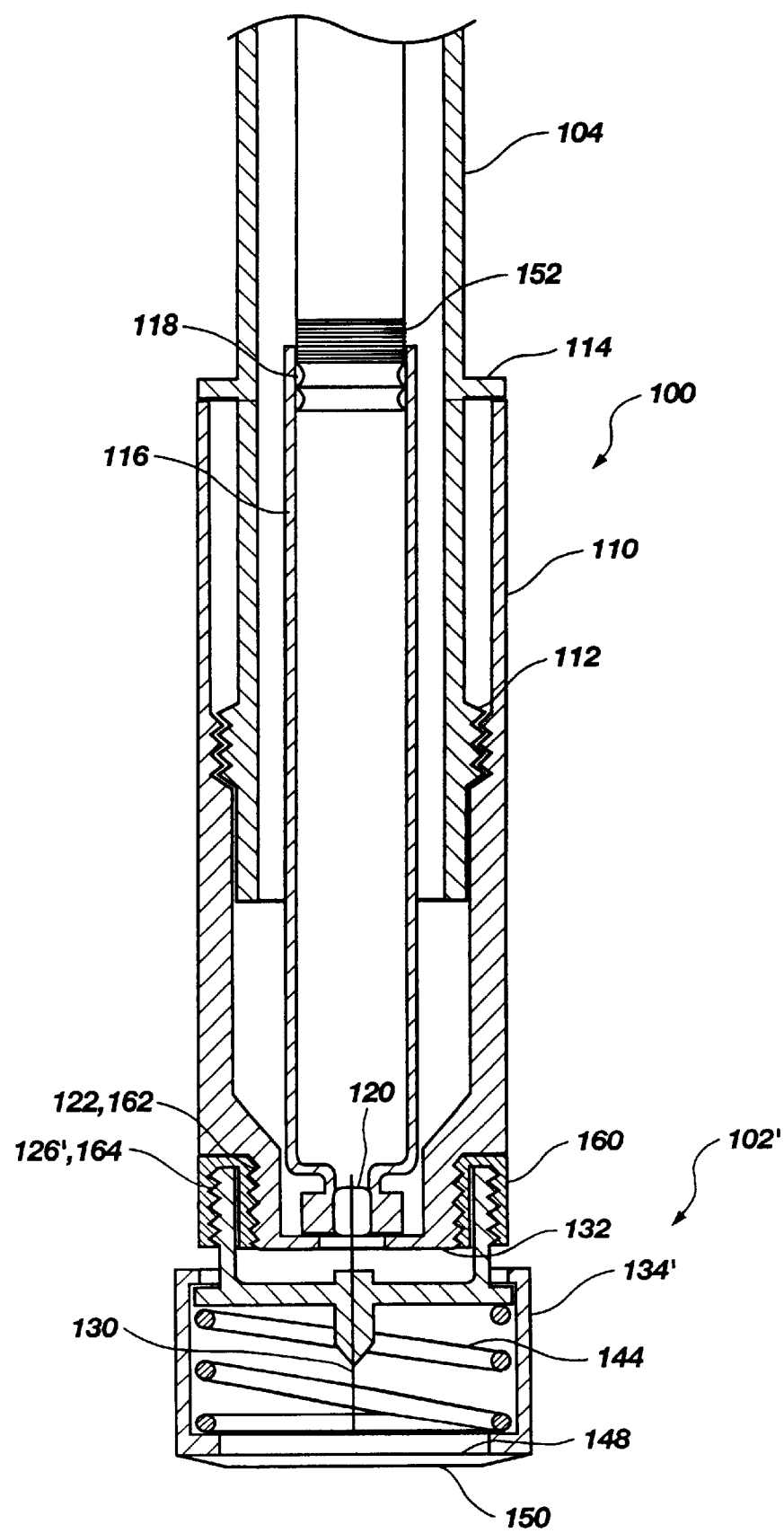
FIG. 8 is a sectional view of the needle assembly and coupling adapter of FIG. 7 operably coupled with an injection device.

As seen in FIG. 8, the coupling adapter 160 is attached to the injection device 100 by way of mating threads 122 and first set of threads 162. The needle assembly 102' is coupled to the coupling adapter 160 by way of an additional set of mating threads 126', 164. Such an arrangement prevents the first membrane 132 from being pinched or stretched between a set of mating threads. Rather, the first membrane 132 is inwardly displaced and positioned between a small annular area formed between the coupling adapter 160 and the upper housing member 124' of the needle assembly 102'. Such an arrangement may provide more efficient manufacturing of the needle assembly by reducing the criticality of the thread tolerances. Also, the risk of tearing the first membrane 132 due to stretching and pinching between mating threads is reduced, if not eliminated, by implementing such a design.

Figure 9:
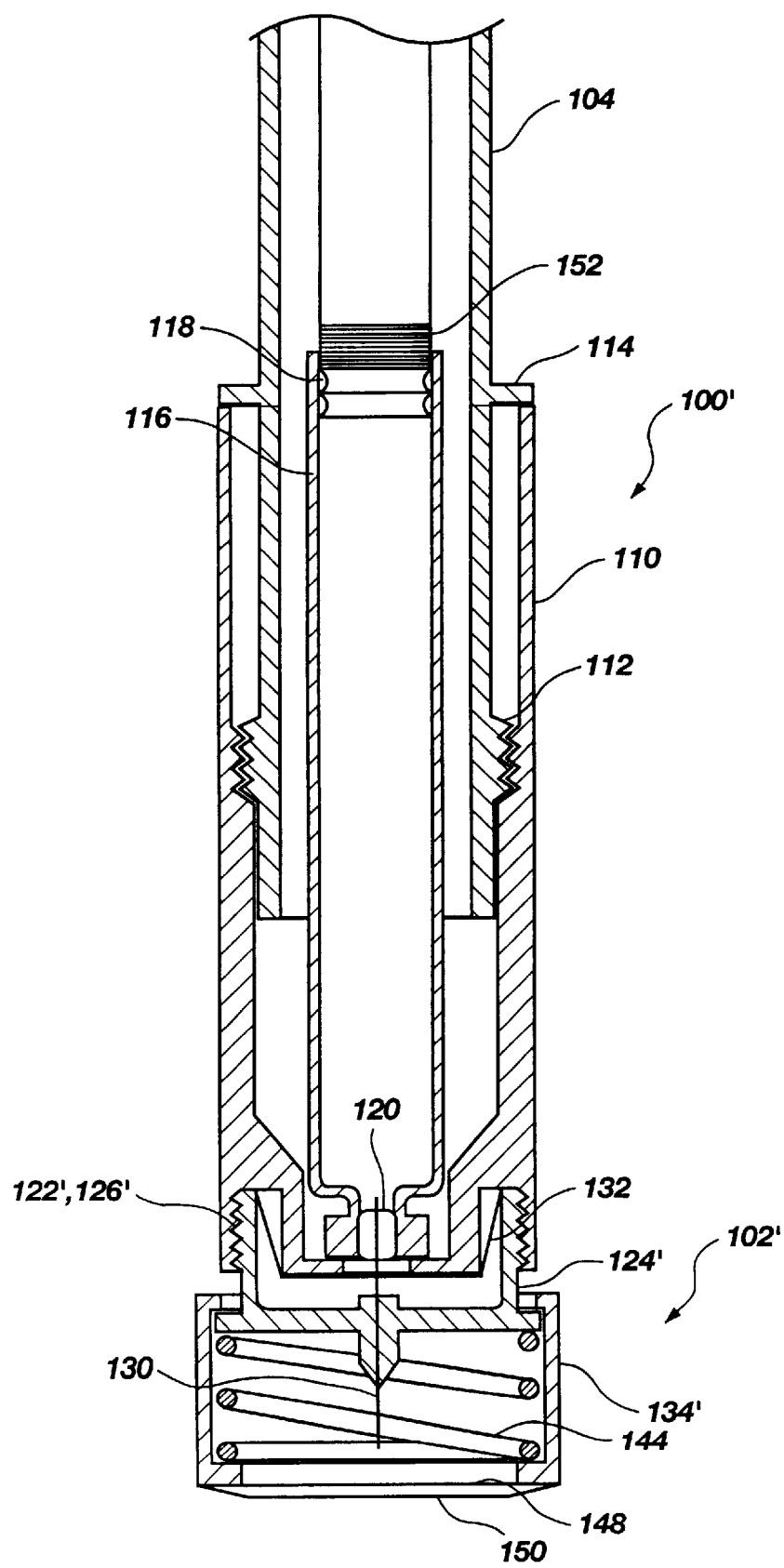
FIG. 9 is a sectional view of a needle assembly operably coupled with an injection device according to another embodiment.

Referring to FIG. 9, the needle assembly 102' described in reference to FIGS. 4 and 5 is shown in use with an alternative injection device 100'. The injection device 100' is similar to the previously described injection device 100 (FIGS. 1, 3A, 3B and 5) except that internal threads 122' are provided on the lower portion 110 for coupling of the needle assembly 102'. This again allows the needle assembly 102' to be coupled to the injection device 100' without placing the first membrane 132 between a mating pair of threads. In fact, such an arrangement may allow for a larger annulus to be formed (i.e., between the upper housing member 124' and the distal end of the injection device 100') in which the displaced first membrane 132 will be positioned, again reducing the likelihood of pinching or tearing.

Figure 10:
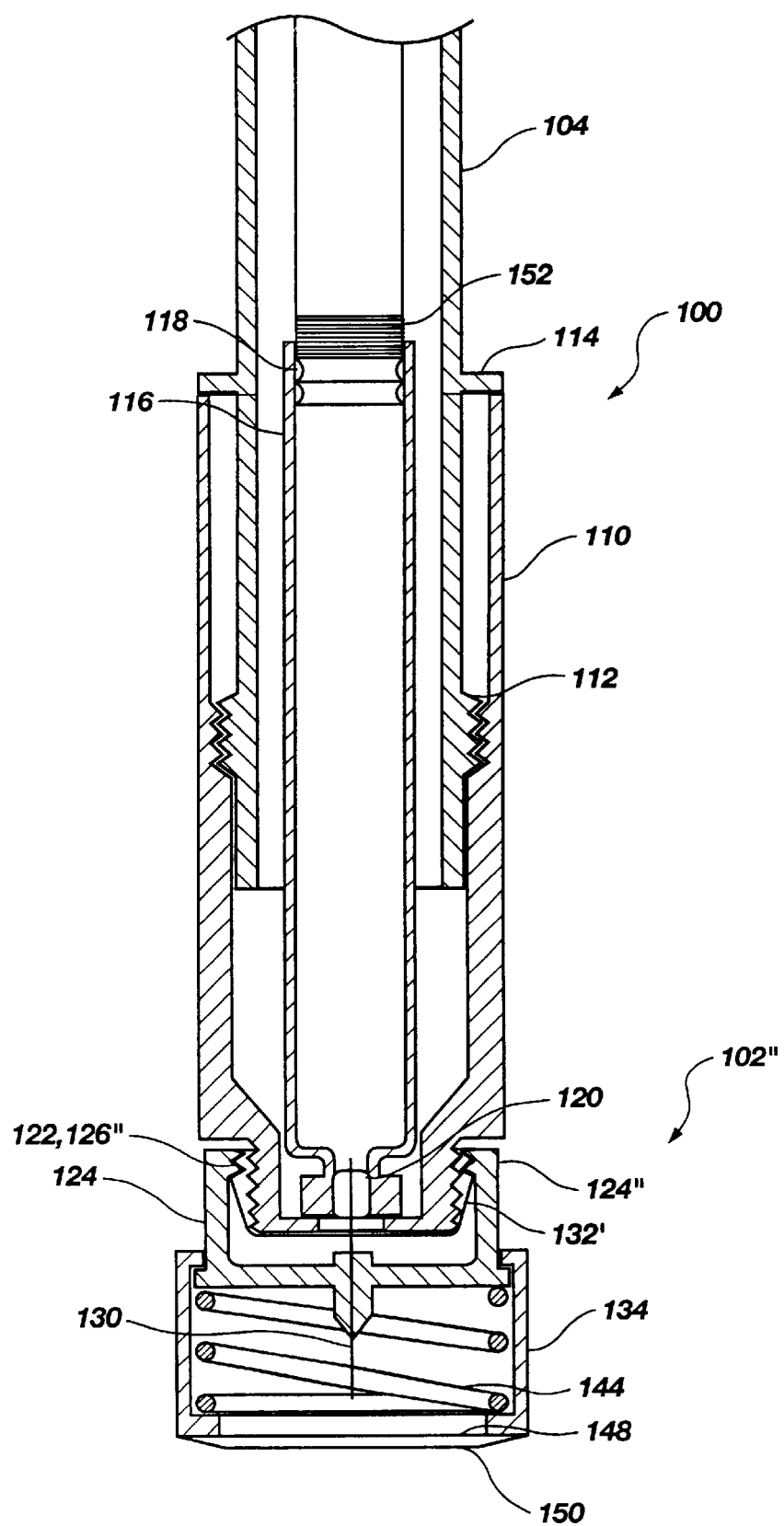
FIG. 10 is a sectional view of a needle assembly operably coupled with an injection device according to yet another embodiment.

Referring to FIG. 10, yet another embodiment of the needle assembly 102" is depicted for use with an injection device 100 having mating threads 122. The needle assembly 102" includes a set of internal threads 126" which are formed only along a partial section within the upper housing member 124". The first membrane 132' is affixed to the upper housing member 124" at a point which is below the last turn of the internal threads 122". This allows the first membrane 132' to be inwardly displaced without being positioned between mating threads 122, 126". Alternatively, the flexible membrane 132' could be affixed in a manner similar to the previously described embodiments. While the first membrane could be positioned between mating threads 122, 126" contact with the same would be reduced since there are a minimal number of engagements between the threads 122, 126".

It is noted that while the embodiments described in conjunction with FIGS. 7 through 10 have not depicted with locking or safety mechanisms, such mechanisms may be incorporated therewith.

Figure 11A:
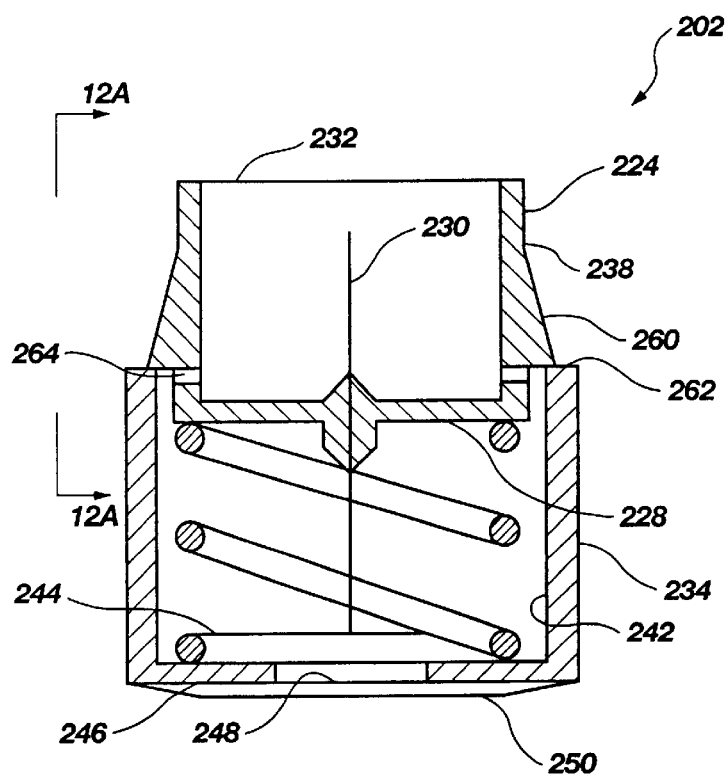
FIGS. 11A through 11C are cross-sectional views of a needle assembly according to another embodiment.
Figure 11B:
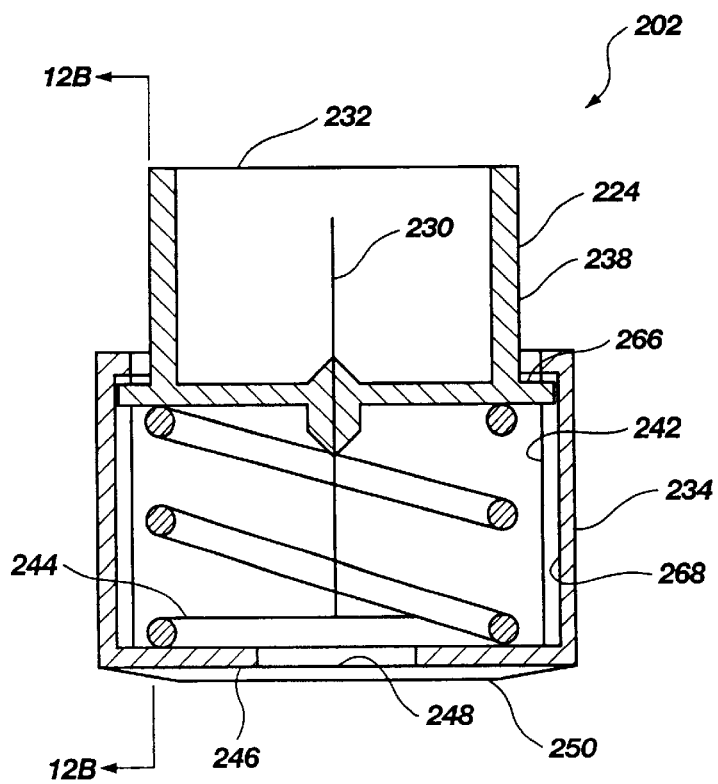
Figure 11C:
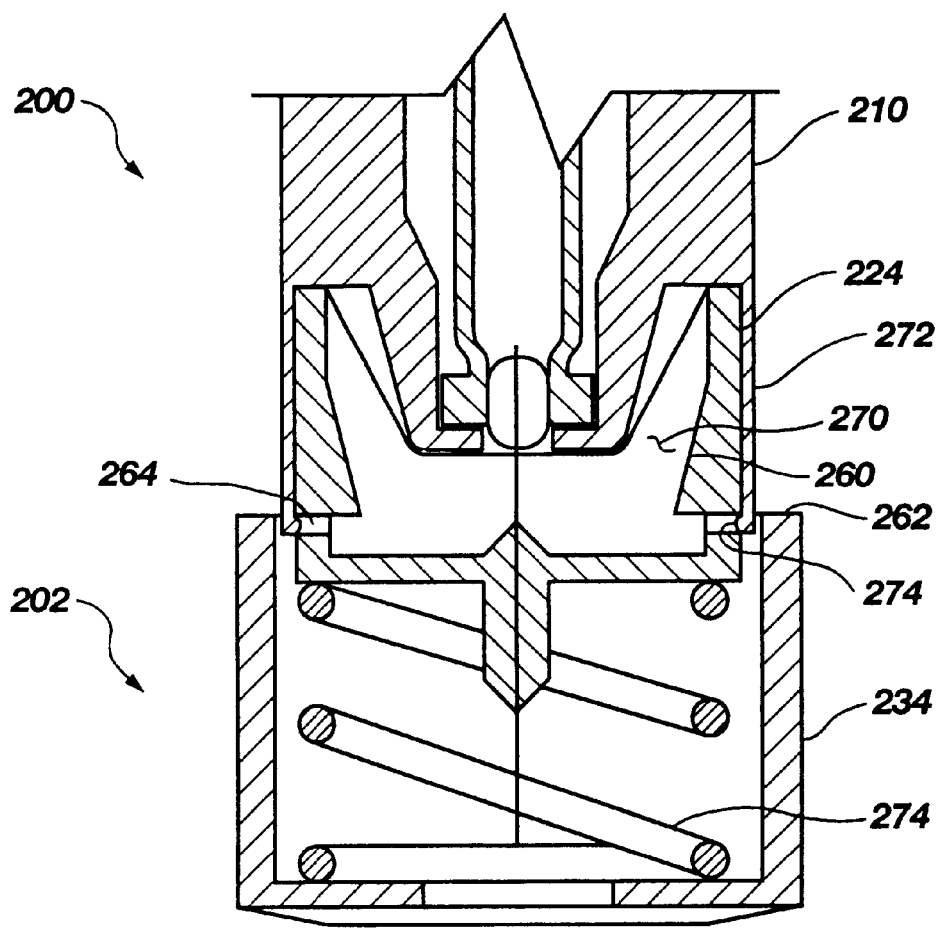

Referring now to FIGS. 11A through 11C, various cross-sectional views of a needle assembly 202 according to another embodiment of the present invention are shown. The needle assembly 202 includes an upper housing member 224 configured for attachment with an injection device 200. The upper housing member 224 includes a support structure 228 for rigidly holding a needle 230, such as a hypodermic needle, relative to the upper housing member 224. A first membrane 232 covers the proximal end of the upper housing member 224 and conceals the needle 230 from access and view of a user when the needle assembly 202 is not coupled with an injection device 200.

A lower housing member 234 is slidably coupled to the upper housing member 224 such that the upper housing member 234 may be rotationally and longitudinally displaced within the lower housing member 234. A biasing member 244, shown as a coil spring, is disposed between the upper housing member 224 and the lower housing member 234, and is configured to keep the needle assembly 202 in an extended position prior to and after an injection. The biasing member 244 also serves to rotationally bias the upper housing member 224 relative to the lower housing member 234 for purposes discussed in greater detail below.

One or more safety members 260 are formed within the side wall 238 of the upper housing member 224. The safety members 260 may include a thickened portion of the side wall 238 that flares outwardly. The safety members 260 act as a locking mechanism by abutting the upper lip 262 of the lower housing member 234 to prevent inadvertent collapse or contraction of the needle assembly 202 prior to coupling of the needle assembly 102 with the injection device 200. Such inadvertent contraction of the needle assembly 202 is to be avoided so as to prevent accidental needle sticks prior to and after use of the needle assembly 202.

Figure 12A:
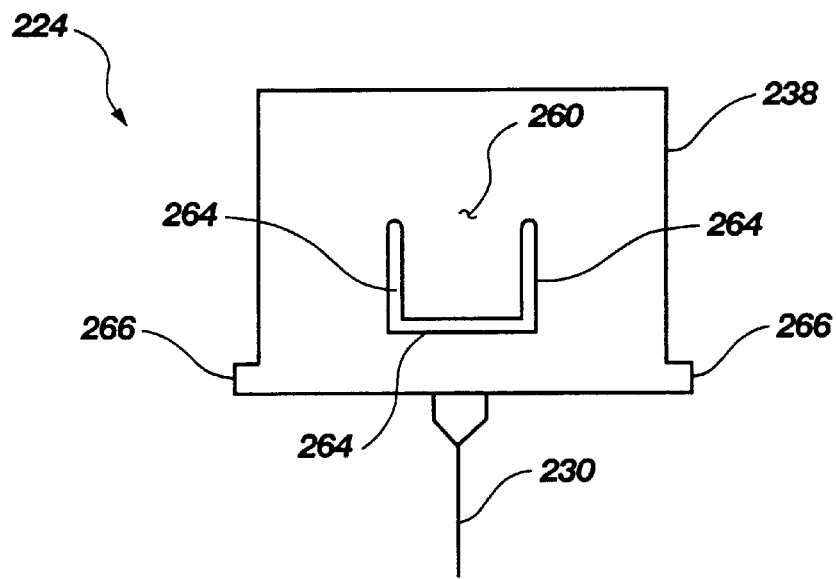
FIGS. 12A and 12B are elevational views showing various features of the needle assembly of FIGS. 11A through 11C.

Referring briefly to FIG. 12A, an elevational view of the upper housing member 224 is shown. The safety member 260 may be formed in the side wall 238 by cutting or otherwise forming one or more grooves 266 about a portion of the safety member 260 which penetrate through the side wall 238 of the upper housing member 224. The grooves 266 allow for flexural disengagement of the safety members 260. While other configurations are contemplated as being within the scope of the invention, the disclosed embodiment includes two safety members 260 formed 180° from each other about the periphery of the upper housing member 224.

Figure 12B:
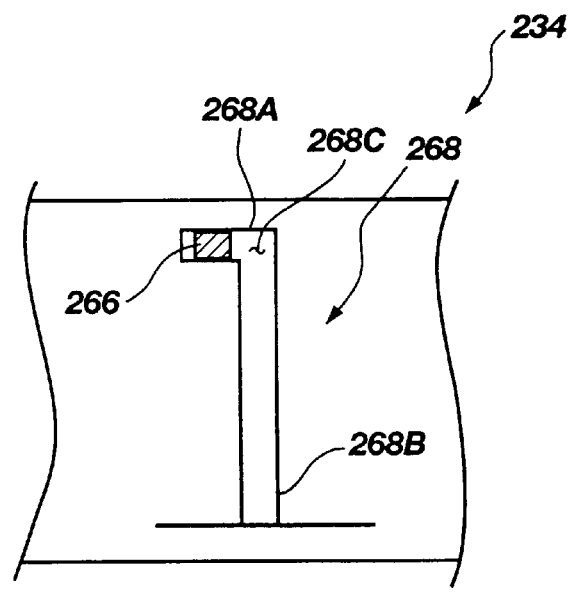

Referring now to FIG. 11B, the needle assembly 202 is shown in a position rotated 90° from that of FIG. 1A. One or more grooves 266 are formed on the lower end of the upper housing member 224. The grooves 266 are positioned in corresponding keyways 268 formed in the interior wall 242 of the lower housing member 234. It noted that FIG. 12A also shows grooves 266 formed at the lower end of the upper housing member 224. Again, while other configurations may be utilized, the two grooves 266 in this particular embodiment are formed 180° from each other and are 90° out of phase with the safety members 260. Referring to FIG. 12B, an elevational view of one of the keyways 268 is illustrated with a corresponding groove 266 positioned therein. The keyway 268 includes a substantially horizontal portion 268A conjoined with a substantially vertical portion 268B, forming a neutral portion 268C. The groove 266 is rotationally biased toward the horizontal portion 268A by the biasing member 244 which keeps the needle assembly 202 in the locked position.

Referring to FIG. 11C, the operation of the safety members 260, as well as the locking mechanism incorporating the grooves 266 and keyways 268, is shown. The needle assembly 202 is coupled to an injection device 200 by inserting the upper housing member 224 into an annulus 270 which is formed at the distal end of the injection device 200. The exterior wall 272 of the annulus 270 fits over the side wall 238 of the upper housing member 224 and forces the safety members 260 inwardly as the needle assembly 202 is inserted into the annulus 270. The safety members 260 are now disengaged such that they no longer abut the upper lip 262 of the lower housing member 234. Thus, the safety members 260 serve to prevent relative longitudinal motion between the upper and lower and upper housing members 224, 234 only while the needle assembly 102 is uncoupled from the injection device 200.

The exterior wall 272 of the annulus may include one or more protrusions 274 for insertion into the grooves 264 about the safety members 260 or in some other groove formed in the upper housing member 224. The positioning of the protrusions 274 into the grooves 264 serves as a locational mechanism and further serves to positively retain the needle assembly 202 on the end of the injection device 200.

After the needle assembly 202 has been coupled to the injection device 200 and the safety members 260 have been disengaged, the lower housing 234 may be rotated relative to the upper housing member 224 such that the groove 266 is rotated out of the horizontal portion 268A of the keyway and into the neutral portion 268C of the keyway. The injection device 200 may then be utilized, as described above with respect to other embodiments, wherein the needle assembly 202 is contracted with the key 266 traveling longitudinally within the vertical portion 268B of the keyway. As previously disclosed, the contraction of the needle assembly 202 serves to introduce the needle 230 into or below the skin of a user such that an injection may be administered.

After an injection has been administered, the biasing member causes the needle assembly 202 to expand, once again concealing the needle 230 therein. Once the groove 266 has reached the neutral portion 268C of the keyway, the biasing member automatically rotates the groove 266 into the horizontal portion 268A of the keyway 268 into the locked position to prevent any subsequent inadvertent needle sticks. If the needle assembly 202 is subsequently uncoupled from the injection device 200 the safety members 260 engage with the upper lip 262 of the lower housing member 234 providing additional protection against inadvertent contraction of the needle assembly 202.

It is further noted that while the aforementioned embodiments have been described as being coupled by means of specific connection types (i.e., threaded or press fit connections), other means of connecting the needle assembly 102 with the injection device 100 are contemplated to be within the scope of the invention. For example, a biased twist-lock type coupling may be utilized. Such a coupling includes a biasing component between the needle assembly 102 and the injection device 200 which allows the device to lock into place upon rotating one component through a nominal angle relative to the other component and resulting in a locking of the two components partially effected by pressure applied by the biasing component. Such coupling devices are known in the art and are not described in further detail herein.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

What is claimed is:

1. An injection needle assembly comprising:
   a first housing member having an opening defined therein;
   a first membrane covering the opening of the first housing member;
   a second housing member having an opening defined therein, the second housing member coupled to the first housing member;
   a second membrane covering the opening of the second housing member; and
   a needle disposed within the first and second housing members such that the needle is concealed by the first and second housing members and the first and second membranes;
   wherein the first housing member is configured to be demountably coupled with an injection device such that the first membrane is displaced inwardly from a first position to a second position upon coupling of the first housing member with the injection device.

2. The injection needle assembly of claim 1, wherein a proximal end of the needle is configured to penetrate the first membrane upon displacement of the first membrane to the second position such that the needle becomes exposed to an interior portion of the injection device.

3. The injection needle assembly of claim 2, wherein the first membrane is configured to substantially return to the first position upon decoupling of the first housing member from the injection device such that the needle is again concealed within the first and second housing members and the first and second membranes.

4. The injection needle assembly of claim 2, wherein the first membrane is configured to plastically deform upon coupling of the first housing member with the injection device.

5. The injection needle assembly of claim 2, wherein the second membrane is configured to be placed upon a portion of a user's skin and wherein a distal end of the needle is configured to penetrate the second membrane and the user's skin upon a lengthwise contraction of the injection needle assembly.

6. The injection needle assembly of claim 5, further comprising a biasing member coupled to the first and second housing members.

7. The injection needle assembly of claim 6, wherein the biasing member effects a lengthwise expansion of the injection assembly upon removal of the second membrane from the user's skin and wherein the needle becomes concealed within the first and second housing members and the first and second membranes upon the lengthwise contraction of the injection needle assembly.

8. The injection needle assembly of claim 2, wherein the first housing member includes a first set of threads for coupling with the injection device.

9. The injection needle assembly of claims 8, wherein the first set of threads are formed on an exterior portion of the first housing member.

10. The injection needle assembly of claim 8, wherein the first set of threads are formed on an interior portion of the first housing member.

11. The injection needle assembly of claim 10, wherein at least a portion of the first set of threads are concealed by the first membrane.

12. The injection needle assembly of claim 1, further comprising a biasing member coupled to the first and second housing members.

13. The injection needle assembly of claim 1, further comprising an antiseptic pad disposed on the second membrane.

14. The injection needle assembly of claim 1, further comprising an anesthetic pad disposed on the second membrane.

15. The injection needle assembly of claim 1, wherein the first and second housing members are substantially cylindrical and wherein the first housing member exhibits a first diameter and the second housing member exhibits a second diameter larger than the first diameter.

16. The injection needle assembly of claim 1, wherein the first and second housing members are formed of plastic.

17. The injection needle assembly of claim 1, wherein the first membrane is formed of polytetrafluoroethylene.

18. The injection needle assembly of claim 1, wherein the first membrane is formed of latex.

19. The injection needle assembly of claim 1, wherein the first membrane is formed of a different material than the second membrane.

20. The injection needle assembly of claim 1, wherein the injection needle assembly is rigidly attached to an interior portion of the first housing member.

21. The injection needle assembly of claim 1, further comprising a locking mechanism configured to prevent inadvertent displacement of the first housing member relative to the second housing member until the injection needle assembly is prepared for use by a user.

22. The injection needle assembly of claim 1, further comprising a first locking mechanism configured to prevent inadvertent displacement of the first housing member relative to the second housing member when the injection needle assembly is not coupled to an injection device.

23. The injection needle assembly of claim 22, wherein the first locking mechanism includes a disposable collar.

24. The injection needle assembly of claim 22, further comprising a second locking mechanism configured to prevent inadvertent displacement of the first housing member relative to the second housing member when the injection needle assembly is coupled to the injection device.

25. The injection needle assembly of claim 24 wherein at least one of the first and second locking mechanisms includes an automatic locking mechanism.

26. The injection needle assembly of claim 24 wherein at least one of the first and second locking mechanisms includes a manual locking mechanism.

27. The injection needle assembly of claim 24 wherein one of the first locking mechanism and second locking mechanism includes an automatic locking mechanism and wherein the other of the first locking mechanism and the second locking mechanism includes a manual locking mechanism.

28. The injection needle assembly of claim 1, further comprising a locking mechanism configured to prevent inadvertent displacement of the first housing member relative to the second housing member when the injection needle assembly is coupled to an injection device.

29. An injection needle assembly comprising:
a first housing member configured to be removably coupled with an injection device;
a first membrane covering an opening at a proximal end of the first housing member;
a second housing member having an opening defined therein, the second housing member coupled to the first housing member and being longitudinally slidable relative the first housing member;
a second membrane covering the opening of the second housing member;
a biasing element disposed between the first housing member and the second housing member; and
a needle rigidly affixed to the first housing member, the needle being disposed within the first housing member and the second housing member and concealed by the first and second membranes;
wherein the first housing member and the first membrane are cooperatively configured such that the first membrane is displaced inwardly from a first position to a second position upon coupling of the first housing member with the injection device.

30. The injection needle assembly of claim 29, further comprising at least one locking mechanism configured to prevent inadvertent displacement of the first housing member relative to the second housing member.

* * * * *